United States Patent
Bader

(10) Patent No.: US 7,915,038 B2
(45) Date of Patent: Mar. 29, 2011

(54) METHOD FOR PRODUCING A RECIPIENT-SPECIFIC TISSUE TRANSPLANT OR TISSUE IMPLANT

(76) Inventor: Augustinus Bader, Immensen (DE)

( * ) Notice: Subject to any disclaimer, the term of this patent is extended or adjusted under 35 U.S.C. 154(b) by 0 days.

(21) Appl. No.: 10/296,672

(22) PCT Filed: May 28, 2001

(86) PCT No.: PCT/DE01/01984
§ 371 (c)(1), (2), (4) Date: Apr. 1, 2003

(87) PCT Pub. No.: WO01/92475
PCT Pub. Date: Dec. 6, 2001

(65) Prior Publication Data
US 2004/0028662 A1 Feb. 12, 2004

(30) Foreign Application Priority Data
May 29, 2000 (DE) .................. 100 26 480

(51) Int. Cl.
*C12N 5/00* (2006.01)
(52) U.S. Cl. .................. 435/325
(58) Field of Classification Search .......... 435/325, 435/347, 366, 373, 384, 395, 1.1
See application file for complete search history.

(56) References Cited

U.S. PATENT DOCUMENTS

| | | | |
|---|---|---|---|
| 4,381,346 A * | 4/1983 | Huasin et al. | 435/215 |
| 4,479,896 A * | 10/1984 | Antoniades | 530/390 |
| 4,878,913 A * | 11/1989 | Aebischer et al. | 623/23.64 |
| 4,890,612 A * | 1/1990 | Kensey | 606/213 |
| 5,192,312 A * | 3/1993 | Orton | 600/36 |
| 5,207,705 A * | 5/1993 | Trudell et al. | 623/1.47 |
| 5,368,858 A * | 11/1994 | Hunziker | 424/423 |
| 5,387,237 A * | 2/1995 | Fournier et al. | 623/23.64 |
| 5,538,722 A | 7/1996 | Blau et al. | |
| 5,716,404 A | 2/1998 | Vacanti et al. | |
| 5,785,964 A * | 7/1998 | Naughton et al. | 424/93.21 |
| 5,804,178 A | 9/1998 | Vacanti et al. | |
| 5,834,308 A | 11/1998 | Peck et al. | |
| 5,843,182 A * | 12/1998 | Goldstein | 128/898 |
| 5,855,610 A | 1/1999 | Vacanti et al. | |
| 5,880,090 A * | 3/1999 | Hammond et al. | 514/2 |
| 5,904,717 A | 5/1999 | Brekke et al. | |
| 6,001,352 A * | 12/1999 | Boyan et al. | 424/93.7 |
| 6,001,647 A | 12/1999 | Peck et al. | |
| 6,001,654 A | 12/1999 | Anderson et al. | |
| 6,074,673 A * | 6/2000 | Guillen | 424/501 |
| 6,197,061 B1 * | 3/2001 | Masuda et al. | 623/11.11 |
| 2003/0170214 A1 | 9/2003 | Bader | |
| 2006/0035374 A1 | 2/2006 | Bader | |
| 2007/0026517 A1 | 2/2007 | Schulz | |
| 2008/0031850 A1 | 2/2008 | Bader | |

FOREIGN PATENT DOCUMENTS

| | | |
|---|---|---|
| EP | 0 564 786 A2 | 10/1993 |
| EP | 0 742 020 A2 | 11/1996 |
| WO | WO 95/24873 | 9/1995 |
| WO | WO 96/08213 | 3/1996 |
| WO | WO 99/00152 | 1/1999 |
| WO | WO 99/27977 | 6/1999 |
| WO | WO 99/52572 | 10/1999 |

OTHER PUBLICATIONS

Wolpe et al. Macrophages secrete a novel heparin-binding protein with inflammatory and neutrophil chemokinetic properties. Feb. 1988. Journal of Experimental Medicine 167: 570-581.*
Aldskogius H et al. 2002. Strategies for repair of the deafferented spinal cord. Brain Res Rev 20:301-308.*
Roskams AJ et al. 2005. Directing stem cells and progenitor cells on the stage of spinal cord injury. Exp Neurol 193: 267-272.*
Daley GQ et al. 2003. Realistic prospects for stem cell therapeutics. Hematol 2003: 398-418.*
Kirschstein R et al. 2001. Can stem cells repair a damaged heart? in Stem cells: scientific progress and future research directions. pp. 87-92.*
Tosh D et al. 2002. Conversion opf pancreatic cells to hepatocytes. Biochem Soc Transact 30: 51-54.*
Pittenger MF et al. 1999. Multilineage potential of mesenchymal stem cells. Science 284: 143-147.*
Steinhauser ML et al. 1998. Macrophage/fibroblast coculture induces macrophage inflammatory protein-1-alpha production mediated by intercellular adhesion molecule-1 and oxygen radicals. J Leuk Biol 64: 636-641.*
Bader et al., "Tissue Engineering of Heart Valves—Human Endothelial Cell Seeding of Detergent Acellularized Porcine Valves," *Eur. J. Cardio-Thoracic Surgery* 14(3):279-284 (1998).
Jaiswal et al., "Osteogenic Differentiation of Purified Culture-Expanded Human Mesenchymal Stem Cells In Vitro," *J. Cellular Biochem.* 64(2):295-312 (1997).
Martin et al., "In Vitro Differentiation of Chick Embryo Bone Marrow Stromal Cells into Cartilaginous and Bone Like Tissues," *J. Orthop. Res.* 16(2):181-9 (1998).
Minuth et al., "Tissue Engineering: Generation of Differentiated Artificial Tissues for Biomedical Applications," *Cell Tissue Res.* 291(1):1-11 (1998).
Niklason et al., "Advances in tissue engineering of blood vessels and other tissues,"*Transplant Immunol.* 5(4):303-306 (1997).
Peter et al., "Osteoblastic Phenotype of Rat Marrow Stromal Cells Cultured in the Presence of Dexamethasone, Beta-Glycerolphosphate, and L-Ascorbic Acid," *J. Cellular Biochem.* 71(1):55-62 (1998).

(Continued)

*Primary Examiner* — L E Barnhart
(74) *Attorney, Agent, or Firm* — Clark & Elbing LLP

(57) ABSTRACT

The method represents a further development of a cell-colonization process, in which biological cells are colonized on a synthetic or natural tissue matrix in order to obtain a tissue implant or tissue transplant. The growth of the cells, which in general come from the designated recipient of the transplant of implant, may be promoted by the addition of mediators, factors or co-factors. The factors or mediators are supplied by co-cultivating cells, which are particularly suitable for producing the factors, with the tissue.

2 Claims, No Drawings

OTHER PUBLICATIONS

Zacchi et al., "In Vitro Engineering of Human Skin-like Tissue," *J. Biomed. Materials Res.* 40(20):187-194 (1998).

Cashdollar et al., "Phenotypic Transformation of the Host Cell Enhances Polyoma Pseudovirion Formation," *Journal of Virology.* 35(3): 895-901 (1980).

Murphy et al., "Phenotypic Transformation of Macrophages to Langerhans Cells in the Skin," *Rapid Communication.* 401-406 (1986).

Schubert et al., "Phenotypic Transformation of Clonal Myogenic Cells to Cells Resembling Chondrocytes," 73(6): 1989-1993 (1976).

van Zoelen et al., "Transforming Growth Factor-β and Retinoic Acid Modulate Phenotypic Transformation of Normal Rat Kidney Cells Induced by Epidermal Growth Factor and Platelet-derived Growth Factor," *The Journal of Biological Chemistry.* 261(11): 5003-5009 (1986).

van Zoelen et al., "The Role of Polypeptide Growth Factors in Phenotypic Transformation of Normal Rat Kidney Cells," *The Journal of Biological Chemistry.* 263(1) 64-68 (1988).

van Zoelen et al., "Phenotypic Transformation of Normal Rat Kidney Cells by Transforming Growth Factor β is not Paralleled by Enhanced Production of a Platelet-Derived Growth Factor," *Eur. J. Biochem.* 209: 89-94 (1992).

Yu et al., "Platelet-Derived Growth Factor (PDGF) Receptor-α Activates c-Jun $NH_2$-terminal Kinase-1 and Antagonizes PDGF Receptor-β-induced Phenotypic Transformation," *The Journal of Biological Chemistry.* 275(25): 19076-19082 (2000).

* cited by examiner

METHOD FOR PRODUCING A RECIPIENT-SPECIFIC TISSUE TRANSPLANT OR TISSUE IMPLANT

The invention relates to a method for preparing a recipient-specific tissue transplant or tissue implant composed of a tissue matrix and recipient-tolerated cells which have colonized it.

In transplantation medicine, there is a great need for suitable transplants which to the smallest possible extent induce adverse reactions in the transplant recipient. Only in certain cases is it possible to remove the transplant from the body of the recipient and graft it back into the recipient. While these transplantations are the safest from the immunological point of view, it is not possible to carry out such transplantations in the case of certain blood vessels or organs or when it is a matter of replacing relatively large areas of the skin. At present, only allogenic transplants from foreign donors or, frequently in the orthopedic field, synthetic implants made from plastics, metals, ceramic, etc., or from various composite materials, are in practice suitable for certain organs. When allogenic materials, such as donor organs, are used, constant immunosuppression, which is stressful for the body of the recipient, is required. Nevertheless, rejection reactions frequently occur as serious complications. Artificial materials can also give rise to rejection reactions and inflammatory processes, which ruin the surgical result.

For various reasons, frequent attempts are nowadays made to use xenogenic material (of animal origin). The particular advantage of this is the greater availability of this material as compared with allogenic (donor) materials. Furthermore, such a "biological material" is more flexible than an artificial material and adapts better to the recipient body at a number of sites. However, xenogenic transplantation material is problematical as a result of being strongly antigenic.

Attempts have therefore been made, form already a relatively long period of time to make xenogenic, allogenic or synthetic transplantation materials, i.e. diverse tissues/fabrics which are intended for a transplantation, recipient-tolerated. To achieve this, attempts are frequently made to colonize xenogenic or allogenic tissues, which are to a large extent immunologically neutralized for the recipient by means of acellularization, or synthetic matrix materials (for example composed of biologically degradable biopolymers) with recipient-tolerated cells in order, in this way, to arrive at a transplant or implant which is, if at all possible, not recognized by the recipient as being foreign to the body or which is at least better tolerated by the recipient on account of the autologous, endogenous cells which are present.

For example, DE 19828726 A1 describes a method for preparing a bioartificial transplant in which native cells are initially removed from the interstitial connective tissue in the transplant. After that, the matrix is freshly colonized with cells which are tolerated by the recipient and which are preferably autologous, such that a recipient-specific biotransplant is obtained.

In order to encourage the cells which are used for the new colonization to grow in a manner resembling that which occurs naturally, and to promote continuous and constant cell renewal, it is advantageous if certain cell mediators or factors which stimulate the growing cells to perform particular processes are supplied to the culture. For example, if the recipient-specific cells which have been applied include fibroblasts, it is then possible to use suitable mediators/factors to stimulate the new formation of collagen and in this way to support transformation of the tissue matrix into a form which is autologous for the recipient. Numerous factors have a chemotactic or growth-accelerating effect, with the skilled person in principle being familiar with the effects of the individual factors in so far as these effects have been investigated. The addition of the factors induces and accelerates said processes and controls them in dependence on the nature and function of the factors.

The procedure which is disclosed in the prior art suffers from the disadvantage that the factors which are used are very expensive. This limits the scope for using the abovementioned methods since preparing recipient-specific transplants or implants by colonizing particular transplant parent structures with recipient-tolerated cells is already very expensive and the method becomes even more expensive as a result of using natural, isolated or synthesized mediators.

Another problem is that of precisely metering in the mediators/factors and cofactors and making sure they are used at times and at sites which are optimal.

The object of the invention is therefore to simplify, reduce the cost of and improve the control of the supply of mediators, factors and cofactors to the tissue culture in a method for preparing a recipient-specific tissue transplant or tissue implant composed of a tissue matrix and recipient-tolerated cells which have colonized it. At the same time, the method should enable the recipient-specific transplant or implant which is obtained to have an even more natural design.

In order to solve this problem, the invention provides, in a method for preparing a recipient-specific tissue transplant or tissue implant composed of a tissue matrix and recipient-tolerated cells which have colonized it, for the colonization of the tissue matrix with the recipient-tolerated cells to be carried out with the participation of additional cells which produce, and release into the environment, mediators, factors or cofactors which promote tissue regeneration.

In the present instance, a "participation" of additional cells which release mediators or factors is to be understood as meaning that these cells, in addition to the recipient-tolerated cells which are used for the colonization within the colonization process, are either introduced directly into the tissue culture and stimulate it to release the mediators and factors by interaction with the recipient-specific cells (such that they intervene directly, and are consequently involved, in the colonization process), or are cultured in parallel to the culture of the tissue transplant or implant within the same culturing device (bioreactor) or cultured simultaneously in a separate apparatus (coculture) with the products (mediators, factors and cofactors) which are secreted into the parallel culture by the cells employed in accordance with the invention being immediately supplied to the tissue culture. The mediators also include inflammation-inducing mediators.

When the cells which release mediators or factors are cultured in parallel, this can take place in a customary culture medium which is suitable for culturing the respective cell type.

Within the context of this invention, "cells which release mediators or cofactors" are understood as meaning those cells which can be comparatively well activated, i.e. stimulated, to release mediators, factors or cofactors which promote tissue regeneration. These cells include, inter alia, macrophages, certain immunocompetent cells, and others. The activation can preferably be effected by means of a stimulus which emanates from the colonizing cells (e.g. cell detritus); alternatively, it can also be effected by adding chemical substances or small foreign particles.

Tissue regeneration is understood as meaning repair processes and processes which involve the breakdown and remodeling of the tissue. The mediator-releasing cells stimulate surrounding cells to carry out transformations which are phenotypic for each cell type, and promote neosynthetic processes and tissue renewal.

Autologous cells belonging to the transplant recipient can be used as cells which release mediators or factors. The following are in particular envisaged: leukocytes, such as lymphocytes, macrophages, granulocytes, dendritic cells and stem cells, in particular pluripotent stem cells or somatic stem cells, or mixtures of these cells. At present, the use of macrophages is regarded as being particularly advantageous.

Particularly when the cells which release mediators or cofactors are cocultured, but also when they are directly added to the transplant tissue culture, these cells can be stimulated to produce particular mediators, factors or cofactors, or to increase the production of these cell products, by means of adding suitable substances. Inter alia, cell detritus from the tissue culture can be used for stimulating the cells.

The method is preferably conducted in such a way that, during the colonization, the cells which release mediators or factors are supplied at least occasionally directly to a culture medium which is used for the colonization and/or to the tissue matrix.

The colonization of the tissue substratum with recipient-tolerated cells to form a tissue transplant or implant can take place in a manner known per se, for example as specified in detail in DE 198 28 726. In this connection, the tissue substratum or tissue matrix, for example a natural or synthetic, acellularized or native collagen matrix or a synthetic fabric, such as a biopolymer fiber structure or biopolymer mesh structure, is generally present in a culture medium which can be supplemented with various additives (also termed conditioning medium; what is meant is the conditioning of the tissue for the colonization). The culture medium can, for example, be agitated above the tissue or be circulated in a circuit above the tissue. The culture medium can also be added at intervals and then left standing over the culture for a period of time; the optimum conditions depend, inter alia, on the type of tissue which is to be colonized.

A customary nutrient medium, which can be provided with various additives, where appropriate, can be used as the culture medium or the conditioning medium. The skilled person is familiar with nutrient media which are suitable for this purpose.

Recipient-specific cells are introduced into the medium either at the beginning of the colonization, continuously or in several batches. "Recipient-specific cells" are understood as being cells which are autologous for the recipient or selected (compatible) allogenic or genetically altered allogenic or xenogenic cells which are as immunologically tolerable as possible for the recipient. Cells can be regarded as being immunologically compatible if tests have classified them as being recipient-like or if they have been adapted to the recipient by being genetically altered, in particular.

It is also possible to feed in different types of cells at different timepoints in the colonization and/or treatment such that different cell layers, composed of different types of cell, can be built up on the tissue. In addition, it is possible to apply different cells locally, for example to apply different cells on the topside and bottomside of a skin transplant or to apply different cells on the inside and the outside of a tubular vessel. In principle, all types of body cells are suitable for use as recipient-tolerated cells, for example:

connective tissue cells (inter alia, fibroblasts and fibrocytes), muscle cells (myocytes), endothelial cells, skin cells (inter alia keratinocytes), cells which have differentiated into organ cells (heart cells, kidney cells, etc.), preferably in the case of structured organs having a collagen scaffolding, and, in general terms, all cells which can usefully be suggested for remodeling a particular tissue which is earmarked for the implantation.

The tissue transplant can in principle be any transplantable tissue. Such tissues include, in particular: generally blood vessels, such as aortas and veins, aortic valves, heart valves, organ parts and whole organs, skin portions, tendons, cornea, cartilage, bone, larynx, heart, trachea, nerves, meniscus, intervertebral disc, ureters, urethra, bladder, etc.

Implants which are based on synthetic matrices or scaffoldings are suitable, among many other possibilities, for veins, heart valves, cornea, bladder and skin.

The cells which release mediators or factors can now, as described above, be supplied at least occasionally to the tissue culture medium and/or the tissue matrix during the colonization. For this purpose, it is possible to apply the cells which release mediators or factors directly to the tissue matrix either once at the beginning of the colonization or together with the recipient-tolerated cells. The cells which release mediators or factors can also be supplied to the culture medium batchwise or continuously, with it also being possible to alternate between culture medium which lacks cells which release mediators or factors and culture medium which contains such cells.

In a further development of the invention, it is also envisaged that blood which naturally contains the desired cells which release mediators or factors, preferably the transplant or implant recipient's own blood, be used for supplying the cells which release mediators or factors. This blood can be concentrated with regard to the desired constituents, or else blood constituents can be separated and then used in this context.

Furthermore preferably, the cells which can be activated for releasing mediators or factors can be maintained in a culture which, during the colonization, is connected to the tissue such that mediators/factors released from the cell culture are supplied to the tissue during the colonization. As described above, it is possible to carry out this coculture of cells which release mediators or factors as a parallel culture outside or within the appliance used for the tissue culture.

The cells which release mediators or factors, for example macrophages, can be cultured in a bioreactor which is connected in a suitable manner to the reactor in which the recipient-specific transplant or implant is being cultured and treated. Factors which are removed from the bioreactor can be supplied in suitable quantity to the conditioning culture medium which is circulating or which is fed batchwise.

Alternatively, the macrophage culture, or the culture of other cells which release mediators or factors, or mixture of cells which release mediators or factors, can be kept separate from the conditioning medium, by means of a film, membrane or partition which is permeable for the cell mediators and/or factors, during the steps of treating with recipient-tolerated cells such that the mediators and/or factors which are formed can be released continuously into the conditioning medium.

The treatment of the tissue earmarked for the transplantation will generally take place in a bioreactor in which the culture medium is kept within a particular space and circulated, where appropriate. A culture space for culturing the cells or macrophages which are used in accordance with the invention can be designed within this space using a permeable partition, such that the cell mediators and/or factors which are formed can migrate continuously into the conditioning medium.

The following can in particular be used as cells which release mediators or factors: cells from the leukocyte family, but also peripheral or central stem cells (derived from blood, fatty tissue, organs and bone marrow), preferably pluripotent stem cells, such as all forms of white blood corpuscles, granulocytes, lymphocytes, macrophages, monocytes, bone marrow cells, spleen cells, memory cells and thymus cells.

In each case, cells or mixtures of cells which are well suited for the given tissue type are selected for the colonization with recipient-tolerated cells. The recipient-tolerated cells, preferably autologous cells, or allogenic or xenogenic cells which have been genetically modified and thereby made recipient-specific, include those cells which are suitable for synthesizing the desired tissue and, in addition, as desired, those cells which can costimulate and/or control the tissue remodeling, such as cells producing cell factors and/or cells having a chemotactic influence, including the abovementioned cells which release mediators or factors.

An advantage of the invention, that is of the participation of cells which produce mediators, factors and cofactors and donate them to the conditioning culture medium, in culturing a transplant or implant which is colonized with recipient-tolerated cells is that mediators/factors which are particularly suitable for the given purpose can be coproduced during a culturing step which is in any case necessary, which means that it is possible to dispense with using additional expensive and less specific factors.

By means of providing particular cells which can be activated for releasing mediators or factors and, where appropriate, by means of suitably stimulating these cells, it is possible to exert an influence on the release of the mediators/factors and in this way control and accelerate the synthesis of the tissue.

Depending on the particular application, the tissue matrix employed can, for example, be a synthetic tissue matrix which can comprise, for example, one or more of the following materials: polyglactide, polydioxanone, biologically degradable polyesters, polyurethanes, polyacrylics, collagen and fibrinogen. It is also alternatively possible, as already described above, to use native or acellularized xenogenic or allogenic tissue matrices.

The invention is described below with the aid of examples:

Accelerated Remodeling of Industrial and Biological Polymers as Carrier Substances (Tissue Matrix) for Novel Bioartificial Tissues Biologically degradable polymers are used as synthetic matrix materials. The synthetic materials can also be purified materials of biological origin. These materials are shaped into "synthetic" matrices (in comparison with acellularized biological tissues). The polymer can be degraded either hydrolytically or enzymically.

It is possible to use biodegradable polymers, such as polyglactide, polydioxanone, polyesters, polyurethanes and polyacrylics, and special biological polymers and (bio)macromolecules, such as collagen or fibrinogen, the classical constituents of extracellular matrix.

In accordance with a customary method, a synthetic tissue substratum (for example a synthetic heart valve) is colonized with the chosen recipient-specific cells. The culture is performed in a medium (e.g. DMBM; WE) which is customary for this purpose. During the colonization, the tissue implant is from time to time flushed, at intervals, with the implant recipient's own blood, with the recipient's own blood which has been concentrated, or with culture medium to which blood constituents have been added. In this phase, macrophages adhere selectively to the exposed matrix. Lymphocytes and macrophages receive immunostimulatory impulses arising from the cleavage products of the polymers and are activated to use endogenous activators to stimulate the autologous myofibroblasts to synthesize matrix. This is particularly important since the, for example hydrolytic, breakdown of the polymers can then take place in an accelerated manner such that this breakdown is substantially shorter than previously possible. This in turn makes it possible to implant a more finished product in vivo without the presence of residual polymers, which, in vivo, are able to induce undesirable instabilities in association with abrupt, accelerated disintegration, or else induce foreign body reactions.

Alternatively to culturing in blood, it is possible to coculture preparations of blood platelets (obtained at approx. 3000 g, with white blood corpuscles being obtained at 1800 g) separately in different regions of the bioreactor or synchronously in a separate apparatus. In the latter case, the culture products which are obtained in this way are supplied to the tissue culture in what is the actual tissue bioreactor.

Inducing a Remodeling in Heart Valves to Give a Normal, Cell-physiological Profile In conventional methods, the phase of preexpanding the vascular cells of the recipient requires approximately 10 days. After that, heart valves are introduced into a bioreactor and, as is customary, colonized luminally using the preexpanded fibroblasts, smooth muscle cells (SMCs) and endothelial cells. In parallel with this, freshly isolated bone marrow stem cells are applied, as a total pool, onto and into the matrix using a syringe. In the matrix, the differentiation of the stem cells is controlled under the local microenvironmental pressure of the spatial position of the extracellular matrix. The activation state of the stem cells is additionally stimulated by matrix cell decomposition products and local cell decomposition products. As a result of using vascular endothelial cells and smooth muscle cells derived from the recipient, interaction takes place with the stem cells. This furthermore generates the tissue-specific cells in situ. This means that, on the basis of taking biopsies, for example when generating heart valves of the aorta, it is necessary to use tissue which cannot be obtained directly from the target tissue. This comprises, for example, venous material, which possesses a molecular and phenotypic differentiation which is different from that of arterial cells derived from the aortic valve. Furthermore, various cell types which are only found, for example, in the valve leaflet, such as neuronal cell systems, are lacking. Under the local micro-environmental pressure of the matrix parameters present in the valve (ideally of an aortic valve matrix which is allogenic, for example) the stem cells differentiate into site-specific cell types including neuronal cell systems which are responsible for local innervation processes. Following the in-vivo implantation, the stem cells can additionally enable repopulation with the arterial cells to take place. However, the ECs are nevertheless important since the thrombogenicity is reduced in the vascular system. The FBs and SMCs, even of venous origin, bring about at least an initiation of the process of remodeling into recipient-specific matrix, with this being continued, corrected and concluded by the cell pools recruited from the stem cells.

The invention claimed is:

1. A method for preparing a recipient-specific tissue transplant or tissue implant, comprising the steps of:
   (a) providing a synthetic matrix onto which cells have been applied that are autologous to the recipient of the transplant or implant and are selected from the group consisting of connective tissue cells, muscle cells, endothelial cells, skin cells, and organ cells selected from heart and kidney cells; and
   (b) cultivating said synthetic matrix of step (a) in a first culture solution that is separated by means of a film, membrane or partition from a second culture, said second culture comprising macrophage that are autologous to the recipient, thereby preparing the recipient-specific implant or transplant.

2. The method as claimed in claim 1, wherein said recipient-specific tissue transplant or tissue implant is a heart valve transplant or a heart valve implant.

* * * * *